(12) United States Patent
Echols

(10) Patent No.: US 6,576,231 B2
(45) Date of Patent: *Jun. 10, 2003

(54) METHODS FOR TREATING HIV-INFECTED PATIENTS BY THE ADMINISTRATION OF GM-CSF AND A PROTEASE INHIBITOR

(75) Inventor: Roger M. Echols, Monroe, CT (US)

(73) Assignee: Schering AG, Berlin (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/928,279

(22) Filed: Sep. 12, 1997

(65) Prior Publication Data

US 2002/0004200 A1 Jan. 10, 2002

(51) Int. Cl.⁷ ............................................. A61K 45/00
(52) U.S. Cl. .................... 424/85.1; 424/85.2; 435/385; 930/140; 930/145
(58) Field of Search .............................. 424/85.1, 85.2; 514/42, 43; 435/385; 930/140, 145

(56) References Cited

U.S. PATENT DOCUMENTS

| | | | | |
|---|---|---|---|---|
| 4,921,837 A | * | 5/1990 | Donahue | 514/2 |
| 5,455,351 A | * | 10/1995 | Kempf et al. | 544/366 |
| 5,492,910 A | | 2/1996 | Barrish et al. | |
| 5,545,640 A | * | 8/1996 | Beaulieu et al. | 514/311 |
| 5,580,769 A | | 12/1996 | Levy et al. | |
| 5,585,397 A | * | 12/1996 | Tung et al. | 514/473 |
| 5,646,180 A | * | 7/1997 | Chaturvedi | 514/471 |
| 5,659,045 A | | 8/1997 | Kempf et al. | |
| 5,665,720 A | | 9/1997 | Young et al. | |
| 5,681,581 A | | 10/1997 | Dunn | |
| 5,691,372 A | * | 11/1997 | Tung et al. | 514/452 |

OTHER PUBLICATIONS

Hammer, et al, "Synergisti Activity of granulocyte. . ." Antimicrob. Agents Chemo. 31(7):1046–1050, 1987.*
Perno, et al, "Replication of human . . ." J. Exp. Med. 169: 933–951, 1989.*
Grossberg, et al, "GM–CSF with ganciclovir for the treatment . . ." NEJM Jun. 8, 1989 p. 1560.*
Groopman, et al, "Effect of recombinant human . . ." NEJM 317: 593–598.*
Pluda, et al., "Subcutaenous recombinant granulocycte–macrophage . . ." Blood 76(3): 463–472, 1990.*
Davey, et al, "A Phase I/II Trial of . . ." J. Infech. Dis. 164: 43–52, 1991.*
Davison, et al, "Quantification of HIV by PCR . . ." J. Clin. Path. 47: 855–857, 1994.*
Deminie et al. Evaluation of reverse transcriptase inhbitors in two–drug combinations against human immunodeficiency virus replication. Antimicrobial Agents and Chemotherapy (1996), pp. 1346–1351.*

The Physicians' Desk Reference, 51 Edition; published by Medical Economics, Inc.; pp. 2291–2294, Dec. 1996.*
Fields et al.; Virology—Third Edition: Lippincott–Raven Publishers; pp. 446–454, Aug. 1996.*
Aber et al., "Delta: a randomised double–blind controlled trial comparing combinations of zidovudine plus didanosine or zalcitabine with zidovudine alone in HIV–infected individuals," Lancet 348(9023):283–291, 1996.
Barbaro, G., et al., "Effect of recombinant human granulocyte–macrophage colony–stimulating factor on HIV–related leukopenia: a randomized, controlled clinical study," Aids 11: 1453–1461, 1997.
Bernstein, Z.P., et al., "A pilot study in the use of GM–CSF in human immunodeficiency virus (HIV) infected individuals,"Blood 90 (suppl. 1):133A, 1997.
Brites, C. et al., "Granulocyte–macrophage–colony–stimulating factor (GM–CSF) reduces viral load and increases CD4 cell counts in individuals with AIDS," Poster presented to the 38$^{th}$ Interscience Conference on antimicrobial Agents and Chemotherapy, September 1998.
Deminie, C.A., "Evaluation of reverse transcriptase and protease inhibitors in two–drug combination against human immunodeficiency virus replication," Antimicrob Agents Chemother 40(6):1346–1351, 1996.
DiMarzio et al., "GM–CSF or CD40L suppresses chemokine response expression and HIV—entry in human monocytes and macrophages," Abstracts of the 5$^{th}$ Conference on Retroviruses and Opportunisitc Infections, p. 86, #37, Feb. 1998.
Folks, T.M. et al., "Cytokine–induced expression of HIV–1 in a chronically infected promonocyte cell line," Science 238:800–802, 1987.
Hammer, S.M., et al., "A trial comparing nucleoside monotherapy with conbination therapy in HIV–infected adults with CD4 cell counts from 200 to 500 per cubic millimeter," N. Engl. J. Med. 335(15):1081–1090, 1996.
Hirsch and D'Aquila, "Therapy for human immunodeficiency virus infection," New England J. of Med, 328(23):1686–1695, 1993.
Mochida, K.N. and Rich, E.A., "Decreased production of human immunodeficiency virus–1 by granulocyte–macrophage colony–stimulating factor unrelated to promotion of DNA synthesis," ALA/ATS 1998 International Conference, Chicago, Illinois, Apr. 1998, Abstract p. A458.
Perno et al., "Effects of bone marrow stiumlatory cytokines on human immunodeficiency virus replication and the antiviral activity of dideoxynucleosides in cultures of monocyte/macrophages,"Blood, 80(4):995–1003, 1992.

(List continued on next page.)

Primary Examiner—James Housel
Assistant Examiner—Ulrike Winkler
(74) Attorney, Agent, or Firm—SEED Intellectual Property Law Group PLLC

(57) ABSTRACT

Provided are methods for inducing an increase in the number of CD4$^+$ T-lymphocytes in HIV-infected patients by administering human GM-CSF. The GM-CSF may be administered concurrently with at least one antiretroviral agent.

6 Claims, No Drawings

OTHER PUBLICATIONS

Perno et al., "Ability of anti–HIV agents to inhibit HIV replication in monocyte/macrophages or U937 monocytoid cells under conditions of enhancement by GM–CSF or anti–HIV antiody," *Aids Research and Human Retroviruses*, 6(8)1051–1055, 1990.

Rusconi, S., et al., "Inhibition of human immunodefinciency virus type 1 replication in cytokine–stimulated monocytes/macrophages by combination therapy," *J. Infect. Dis.* 170: 1361–1366, 1994.

Saravolatz, L.D., et al., "Zidovudine alone or in combination with didanosine or zalcitabine in HIV–infected patients with the acquired immunodeficiency syndrome or fewer than 200 CD4 cells per cubic millimeter," *Engl. J. Med.* 335(15):1099–1106, 1996.

Skowron, G. et al., "Safety and Anti–HIV effect of GM–CSF in patients on highly active anti–retroviral therapy," $5^{th}$ Annual Conference on Retroviruses & *Opportunistic Infect*, Chicago, IL, Feb. 1–5, 1998.

New Clinical Data Indicates LEUKINE Maintains Viral Suppression and Extends Duration of Antiretroviral Therapy Utility in People with AIDS, Immunex Corporation press release, May 3, 1999.

AMFAR (American Foundation for AIDS Research) AIDS/HIV Treatment Directory Vol. 7, No. 3, list of clinical trials and study locations, June 1994.

Immunex Annual Report, Product Pipeline, p. 10, 1995.

"Available HIV/AIDS Drugs Update," British Columbia Center for Excellence in HIV/AIDS, St. Paul's Hospital, Vancouver, BC, *Forecast*, Dec. 1995.

"HIV, AIDS and Injection Drug Use: A National Action Plan," British Columbia Center for Excellence in HIV/AIDS, St. Paul's Hospital, Vancouver, BC, *Forecast*, pp. 1 and 7–11, Mar. 1998.

Frumkin, "Role of granulocyte colony–stimulating factor and granulocyte–macrophage colony–stimulating factor in the treatment of patients with HIV infection," *Current Opinion in Hematology* 4: 200–206 (1997).

CTN (Canadian HIV Trials Network), University of British Columbia/St. Paul's Hosiptal, Vancouver, BC, *Network Update*, vol. 6, No. 2, pp. 1–3, Mar./Apr. 1995.

Bender, A., et al., "Effect of granulocyte/macrophage colony–stimulating factor on human monocytes infected with influenza A virus,"*J. Immunol.* 151: 5416–5424, 1993.

Crowe, S. and Lopez, A., "GM–CSF and its effects on replication of HIV–1 in cells of macrophage lineage", *J. Leukoc. Biol.* 62: 41–48, 1997.

Davey, R., et al., "A phase I/II trial of zidovudine interferon–α, and granulocyte–macmacrophage colony–stimulating factor in the treatment of human innunodefiency virus type 1 infection," *J. Infect. Dis.* 164: 43–52, 1991.

Davidson, F., et al., "Quantification of HIV by PCR in monocytes and lymphocytes in patients receiving antiviral treatment and low dose recombinant human granulocyte macrophage colony stimulating factor," *J. Clin. Pathol.* 47: 855–857, 1994.

DiMarzio, P., et al. "Chemokine receptor regulation and HIV type 1 tropism in monocyte–macrophages," *Aids Res. Hum. Retroviruses* 14: 129–138, 1998.

Dorr, R., "Clinical properties of yeast–derived versus *Escherichia coli*–derived granulocye–macrophage colony-stimulating factor," *Clin. Ther.* 15: 19–29, 1993.

Fletcher, M. and Gasson, J., "Enhancement of neutrophil function by granulocyte–macrophage colony–stimulating factor involves recruitment of a less responsive subpopulation,"*Blood* 71: 652–658, 1988.

Foli, A., et al., "Effects of the $Th_1$ and $Th_2$ stimulatory cytokines interelukin–12 and interleukin–4 on human immunodeficiency virus replication," *Blood* 85: 2114–2123, 1995.

Groopman, J., et al., "Effect of recombinant human granulocyte–macrophage colony–stimulating factor on myelopoiesis in the acquired immunodeficiency syndrome," *N. Engl. J. Med.* 317:593–598, 1987.

Grossberg, H., and Bonnem, E., "GM–CSF with ganciclovir for the treatment of CMV retinitis in AIDS," Abstract *N. Engl. J. Med.:* 1560, 1989.

Hammer, S. and Gillis, J., "Synergistic activity of granulocyte–macrophage colony–stimulating factor and 3'–azido–3'–deoxythymidine against human immunodeficiency virus in vitro," *Antimicrob. Agents Chemother.* 31: 1046–1050, 1987.

Hammer, S., et al., "In vitro modification of human immunodeficiency virus infection by granulocyte–macrophage colony–stimulating factor and γ interferon," *Proc. Natl. Acad. Sci. USA* 83: 8734–8738, 1986.

Hammer, S., et al., "Effect of zidovudine and granulocyte–macrophage colony–stimulating factor on human immunodeficiency virus replication in alveolar macrophages," *Blood* 75: 1215–1219, 1990.

Hardy, D., et al., "Combination of ganciclovir and granulocyte–macrophage colony–stimulating factor in the treatment of cytomegalovirus retinitis in AIDS patients," *Eur. J. Clin. Microbiol. Infect. Dis.* 13: S34–S40, 1994.

Hermans, P., "Haematopoietic growth factors as supportive therapy in HIV–infected patients,"*AIDS 9 Suppl* 2: S9–S14, 1995.

Hermans, P., et al., "Possible role of granlocyte–marophage colony stimulating factor (GM–CSF) on the rapid progression of AIDS–related Kaposi's sarcoma lesions in vivo," *Br. J. Haematol.* 87(2): 413–414, 1994.

Hewitt, R., et al., "Pharmacokinetics and pharmacodynamics of granulocyte–macrophage colony–stimuating factor and zidovudine in patients with AIDS and severe AIDS–related complex," *Antimicrob. Agents Chemother.* 37: 512–522, 1993.

Hovgaard, D., et al., "Comparative pharmacokinetics of single–dose administration of mammalian and bacterially-derived recombinant human granulocyte–macrophage colony–stimulating factor," *Eur. J. Hematol.* 50: 32–36, 1993.

Kaplan, L., et al., "Clinical and virologic effects of recombinant human granulocyte–macrophage colony–stimulating factor in patients receiving chemotherapy for human immunodeficiency virus–associated non–Hodgkin's lymphoma: results of a randomized trial," *J. Clin. Oncol.* 9: 929–940, 1991.

Koyanagi, Y., et al., "Cytokines alter production of HIV–1 primary mononuclear phagocytes," *Science* 241: 1673–1675, 1988.

Krown, S.E., et al., "Interferon–α, zidovudine, and granulocyte–macrophage colony–stimulating factor: a phase I AIDS clinical trials group study in patients with Kaposi's sarcoma associated with AIDS," *J. Clin. Oncol.* 10: 1344–1351, 1992.

Levine, J., et al., "Recombinant human granulocyte–macrophage colony–stimulating factor ameliorates zidovudine–induced neutropenia in patients with acquired immunodeficiency syndrome (AIDS)/AIDS–related complex," *Blood* 78: 3148–3154, 1991.

Lieschke, G., and Burgess, A., "Granulocyte colony–stimulating factor and granulocyte–macrophage colony–stimulating factor," *N. Engl. J. Med.* 327: 28–35, 1992.

Matsuda, S., et al., "Suppression of HIV replication in human monocyte–derived macrophages induced by granulocyte/macrophage colony–stimulating factor," *Aids Res. Hum. Retroviruses* 11: 1031–1038, 1995.

May, A., et al., "Crystal structure of the N–terminal domain of sialoadhesin in complex with 3' sialyllactose at 1.85 Å resolution," *Mol. Cell* 1: 719–728, 1998.

Miles, S., et al., "Combined therapy with recombinant granulocyte colony–stimulating factor and erythropoietin descreaes hematologic toxicity from zidovudine," *Blood* 77: 2109–2117, 1991.

Mitsuyasu, R., "Clinical uses of hematopoietic growth hormones in HIV–related illnesses," *Aids Clin. Rev.:* 189–212, 1993/1994.

Perno, C., et al., "Activity of GM–CSF and M–CSF upon replication of HIV and other DNA–and RNA–viruses in primary macrophages," Program and Abstracts of the 3rd Conference on Retroviruses and Opportunistic Infections, Washington, D.C., 1996.

Perno, C., et al., "Replication of human immunodeficiency virus in monocytes,"*J. Exp. Med.* 169: 933–951, 1989.

Pluda, J., et al., "Subcutaneous recombinant granulocyte–macrophage colony–stimulating factor used as a single agent and in an alternating regimen with azidothymidine in leukopenic patients with severe human immunodeficiency virus infection," *Blood* 76: 463–472, 1990.

Pluda, J., et al., "Hematologic effects of AIDS therapies," *Hematol. Oncol. Clin. North Am.* 5: 229–248, 1991.

Scadden, D., et al., "Granulocyte–macrophage colonystimulating factor mitigates the neutropenia of combined interferon alfa and zidovudine treatment of acquired immune deficiency syndrome–associated Kaposi's sarcoma," *J. Clin. Oncol.* 9: 802–808, 1991.

Scadden, D., et al., "Lack of in vivo effect of granulocyte–macrophage colony–stimulating factor on human immunodeficiency virus type 1," *Aids Res. Hum. Retroviruses* 12: 1151–1159, 1996.

Stricker, R. and Goldberg, B., "Increase in lymphocyte subsets following treatment of HIV–associated neutropenia with granulocyte colony–stimulating factor," *Clin. Immunol. Immunopathol.* 79:194–196, 1996.

Leukine (Sargramostim) A recombinant GM–CSF yeast–expressed, Product Monograph, 1–20.

* cited by examiner

METHODS FOR TREATING HIV-INFECTED PATIENTS BY THE ADMINISTRATION OF GM-CSF AND A PROTEASE INHIBITOR

FIELD OF THE INVENTION

The subject invention relates to methods for increasing the number of circulating $CD4^+$ T-lymphocytes in HIV-infected patients by the administration of granulocyte-macrophage colony stimulating factor (GM-CSF).

BACKGROUND OF THE INVENTION

Patients infected with Human Immunodeficiency Virus (HIV) experience a variable but progressive decline in immune function resulting in clinically apparent opportunistic infections and other diseases. (Crowe et al., *J. Acquir. Immune Defic. Syndr.* 4:770–76, 1991; Moss et al., *AIDS* 3:55–61, 1989). The onset of severe immunodeficiency in HIV-infected individuals is generally accompanied by a marked increase in viral load and a dramatic decline in circulating $CD4^+$ T-lymphocytes. Indeed, one of the clinical criteria for the diagnosis and reporting of AIDS (as established by the Centers for Disease Control and Prevention) is a decrease in the number of $CD4^+$ T-lymphocytes to <200 cells/mL. (Normal $CD4^+$ T-lymphocyte cell counts in healthy $HIV^-$ individuals range between 800 and 1600 cells/mL.) $CD4^+$ T-lymphocytes perform multiple immune-modulating functions. The decline in $CD4^+$ T-lymphocytes, and decline in cell-mediated immunity, is the primary factor responsible for the susceptibility of HIV-infected patients to many opportunistic infections characteristic of the adult immunodeficiency syndrome, or AIDS. Accordingly, an increase in $CD4^+$ T-lymphocytes is generally regarded as an indicator of efficacy for anti-HIV drugs.

Inhibition of HIV replication can increase $CD4^+$ T-lymphocyte counts. Such antiretroviral therapy typically involves combinations of drugs such as protease inhibitors, nucleoside analogs, and non-nucleoside reverse transcriptase inhibitors. Other agents, including biologics, have also demonstrated some antiviral effects. The decrease in viral load is generally, but not always, associated with an increase in the number of circulating $CD4^+$ T-cells. (Yarchoan et al., *Ann Intern. Med.* 115:184–89, 1991; Hirsch and D'Aquila, *N. Engl. J. Med.* 328:1686–95, 1993; Volberding, P. A., In: Crowe et al., eds., *Management of the HIV-Infected Patient*, pp. 53–63). Unfortunately, antiretroviral drugs do not result in complete reconstitution of the immune function. Moreover, inhibition of viral replication by these agents is temporary, due to the evolution of resistant strains of virus that can grow in the presence of the antiretroviral agents. (Cameroni et al., Third Human Retroviral Conference, January 1996, Abstract #LB6a).

Growth factor cytokines such as granulocyte-colony stimulating factor (G-CSF), granulocyte-macrophage colony stimulating factor (GM-CSF), and erythropoietin (EPO) have also been administered to patients with HIV. (Scadden et al., 1991, Levine et al., *Blood* 73:3148–54, 1991; Kaplan et al., *J. Clin. Oncol.* 9:929–40, 1991; Stricken and Goldberg, *Clin. Immunol. Immunopathol.* 79:194–96, 1996; Miles et al., *Blood* 77:2109–17, 1991; Pluda et al., *Hematol. Oncol. Clin. North Am.* 5:229–48, 1991). Recently, GM-CSF has been the subject of several studies to evaluate its ability to prevent opportunistic infections in individuals with HIV.

LEUKINE®, a yeast-derived form of GM-CSF, is currently available for use in promoting myeloid cell recovery following bone marrow transplant post-myeloablative therapy for the treatment of malignancies. An *E. coli*-derived form of GM-CSF is also available for use in promoting the recovery of neutrophils in HIV-infected patients with granulocytopenia. (Scadden et al., *J. Clin. Oncol.* 9:802–08, 1991; Levine et al., *Blood* 78:3148–54, 1991; Kaplan et al., *J. Clin. Oncol.* 9:929–40, 1991; Hardy et al., *Eur. J. Clin. Microbiol. Infect. Dis.* 13:S34–S40, 1994). However, the widespread use of GM-CSF for treatment of HIV infection has been hindered by data from in vitro studies whose results suggest that this cytokine might actually enhance HIV replication (Bender et al., *J. Immunol.* 151:5416, 1993; Foli et al., *Blood* 8:2114, 1995; Pluda et al., *Hematol. Oncol. Clin. North Am.* 5:229–48, 1991). More recent studies have reported results which are inconsistent with earlier studies with regard to the effect of GM-CSF on HIV viral replication (Perno et al., Third Human Retroviral Conf., January 1996, Abstract #463; Pluda et al., *Blood* 76:463–72, 1990; Fletcher and Gasson, *Blood* 71:652–58, 1988; Mitsuyasu, R. T. In: Volberding and Jacobson, eds. *AIDS Clinical Review*, N.Y., N.Y. 1993–94, pp. 189–212). It is now believed that in the presence of antiretroviral therapy, GM-CSF does not upregulate HIV viral replication. (Scadden et al., 1995; Davison et al., *J. Clin. Pathol.* 47:855–57, 1994, Scadden et al., *AIDS Res. and Human Retroviruses* 12:1151–59, 1996). Indeed, in vitro data have demonstrated the enhancement of AZT activity by GM-CSF due to increased intracellular concentration of the active triphosphorylated form of AZT. (Hammer and Gillis, *Antimicrob. Agents Chemother.* 31:1046–50, 1987).

Developing effective therapies for HIV disease has presented a formidable challenge for medical researchers. Although significant advancements have been made in the treatment of HIV-infected patients, many patients remain untreatable due to ineffectiveness of the therapeutic drugs used or inability of the patients to tolerate the side effects of the therapies. Clearly, existing therapies do not yet offer a cure to HIV disease. Immune-modulating agents, such as GM-CSF, may therefore offer an additional alternative treatment.

SUMMARY OF THE INVENTION

The present invention provides methods for increasing $CD4^+$ lymphocyte counts in HIV-infected patients by the therapeutic administration of GM-CSF. This method of treatment has been demonstrated to induce an increase in the absolute number of circulating $CD4^+$ T-lymphocyte cells in patients concurrently receiving antiretroviral drugs, with no significant increase in viral load.

This invention is based on the results of a double-blinded, placebo-controlled study that enrolled HIV-infected patients at two study sites. In this study, patients receiving anti-retroviral agents for a minimum of eight weeks prior to study received therapeutically effective amounts of recombinant human GM-CSF or placebo. Viral load and $CD4^+$ T-lymphocyte counts were determined twice prior to the start of the study (baseline), then two weeks, four weeks, and eight weeks after the start of the study, and twice approximately four weeks after the treatment phase was completed. Results indicated that within the placebo arm of the study, there was no significant change in the median values for $CD4^+$ T-cell counts relative to the baseline. Within the GM-CSF arm of the study, a trend towards an increase in the median value for $CD4^+$ T-lymphocyte counts was observed between the baseline and all evaluations during the course of the study.

DETAILED DESCRIPTION OF THE PREFERRED EMBODIMENT

The present invention provides methods for inducing an increase in the number of $CD4^+$ T lymphocytes in an HIV-infected patient by administering therapeutically effective amounts of granulocyte-macrophage stimulating factor (GM-CSF).

In accordance with the present invention, GM-CSF is administered to HIV-infected patients in amounts and for a time sufficient to induce a clinically significant increase in the patient's $CD4^+$ T-lymphocyte count. A "$CD4^+$ T-lymphocyte count" means the number of circulating $CD4^+$ T-lymphocytes in the patient's blood, expressed as $CD4^+$ T-lymphocyte cells per unit volume. Generally, $CD4^+$ lymphocyte counts are expressed as cells/$mm^3$ of whole blood. An increase in the $CD4^+$ T-lymphocyte count is defined as a rise relative to the baseline (i.e., before administration of GM-CSF) value. For the purposes of the present invention, a "clinically significant" increase in $CD4^+$ T-lymphocyte cells is an increase of greater than or equal to about 30% of the baseline value.

GM-CSF used in the practice of the invention includes any pharmaceutically safe and effective human GM-CSF, or any derivative thereof having the biological activity of human GM-CSF. In a presently preferred embodiment, the GM-CSF used in the practice of the subject methods is recombinant human GM-CSF (rhu GM-CSF), such as LEU-KINE® (Immunex Corporation, Seattle, Wash.). LEUK-INE® is a biosynthetic, yeast-derived, recombinant human GM-CSF, consisting of a single 127 amino acid glycoprotein that differs from endogenous human GM-CSF by having a leucine instead of a proline at position 23. Other natural and synthetic GM-CSFs, and derivatives thereof having the biological activity of natural human GM-CSF, will of course be equally useful in the practice of the invention.

As the degree of glycosylation of biosynthetic GM-CSFs appears to influence half-life, distribution, and elimination, the most effective dose of GM-CSF for the subject methods may vary depending on the source used (Lieschke and Burgess, *N. Engl. J. Med.* 327:28–35, 1992; Dorr, R. T., *Clin. Ther.* 15:19–29, 1993; Horgaard et al., *Eur. J. Hematol.* 50:32–36, 1993). The optimal dose of GM-CSF used for LEUKINE® may be adjusted if a GM-CSF other than LEUKINE® is used to induce $CD4^+$ T-lymphocyte cells in HIV-infected patients.

LEUKINE® has been shown to exhibit the same hematopoietic effects as those induced by endogenous GM-CSF, namely, the stimulation of progenitor cells committed along the granulocyte-macrophage pathway to form neutrophils, monocytes, macrophages, and eosinophils (Technical Product Report: LEUKINE® Liquid, Immunex Corp., Seattle, Wash., 1997, which is herein incorporated by reference). LEUKINE®, like endogenous GM-CSF, also promotes the differentiation of progenitor cells giving rise to erythrocytes and megakaryocytes (Ibid.) In addition to stimulating hematopoiesis, LEUKINE® enhances many of the functional activities of mature neutrophils, monocytes and macrophages, such as chemotaxis, growth factor secretion, anti-tumor activity, antibacterial and antifungal activities, and so on (Ibid.).

Various embodiments of the subject invention are disclosed herein. In one preferred embodiment, GM-CSF may be administered concurrently with antiretroviral agents, including, but not limited to, nucleoside reverse transcriptase inhibitors, non-nucleoside reverse transcriptase inhibitors, or protease inhibitors. The term "antiretroviral agent", as used herein, includes any pharmacological, biological or cellular agent that has demonstrated the ability to inhibit HIV replication. Specific examples of nucleoside reverse transcriptase inhibitors include zidovudine (AZT), didanosine (ddI), lamivudine (3TC), stavudine (d4T), and dalcitabine (ddC). Specific examples of non-nucleoside reverse transcriptase inhibitors include nevirapine and delavirdine. Specific examples of protease inhibitors include indinavir, nelfinavir, ritonavir, and saquinavir. Patients treated in accordance with the present invention may be treated concurrently with one or more anti-retroviral agents. Additional antiretroviral agents not yet approved by the Food and Drug Administration may also be effective.

The optimal dose, frequency of administration, and duration of treatment with GM-CSF which is effective to induce a clinically significant increase in $CD4^+$ T-lymphocyte counts may vary from patient to patient. Generally, however, therapeutically effective doses of GM-CSF sufficient to induce an increase in the patient's $CD4^+$ T-lymphocyte count will be greater than or equal to about 100 micrograms (mcg). Preferably, doses of GM-CSF will be greater than or equal to about 150 mcg, and more preferably, doses of GM-CSF will be greater than or equal to about 250 mcg.

In preferred embodiments of the present invention, GM-CSF is administered for a period of time greater than about three weeks, and more preferably greater than about four weeks, at a frequency of at least two times per week, more preferably at least three times per week, and most preferably once per day or more. However, it should be understood that the optimal dose and length of treatment may vary from patient to patient, depending on the individual patient's condition and response to the treatment, and is best determined by monitoring the patient's response during the course of the treatment. It should further be understood that administration of higher doses may permit less frequent administration, and lower doses may require more frequent administration in order to achieve clinically significant increases of $CD4^+$ T-lymphocyte counts. A treatment regimen (dosage amount, frequency and duration) is therapeutically effective if it results in a clinically significant increase in $CD4^+$ T-lymphocyte counts.

The methods of the subject invention thus include inducing an increase in the $CD4^+$ T-cell count in an HIV-infected patient who may also be treated with an antiretroviral agent in which the patient is administered an amount of GM-CSF sufficient to induce an increase in the patient's $CD4^+$ T-lymphocyte count.

EXAMPLE

Study Design

A study was conducted to determine the safety and efficacy of human GM-CSF as a therapeutic reagent in HIV-infected patients. Because some in vitro studies had indicated the possibility that GM-CSF might enhance HIV replication in vivo, this study assessed the impact of co-administration of GM-CSF with an antiretroviral agent on HIV replication. HIV viral burden was measured by the RNA-PCR (AMPLICOR®) method. To assess the effects of this treatment on lymphocyte counts, blood samples were analyzed throughout the study for determination of $CD3^+$, $CD4^+$, and $CD8^+$ T-lymphocyte counts.

This study was a Phase I/II, randomized, double-blind, placebo-controlled, two-center trial involving patients with HIV disease. Patients meeting specific entry criteria were randomized to treatment with GM-CSF or placebo, and these were administered by subcutaneous injection three times per week for eight weeks. Viral load was determined at baseline (mean of three determinations within fourteen days of study entry), then at two weeks, four weeks, and eight weeks after starting study drugs, and on two separate occasions approximately four weeks after the conclusion of the treatment phase (post-treatment evaluation). Clinical and lymphocyte subset evaluations were performed at each of these same time points (i.e., pre-treatment, week 2, week 4, week 8, and 4 weeks post-study). Twenty patients were enrolled in the study, ten per treatment arm. All twenty patients completed the study.

Patients were eligible for inclusion in the study if the following parameters were met: documented HIV infection, including detectable RNA-PCR during baseline evaluation period, age $\geq 18$ years (or legal age of consent), adequate hematologic function, satisfactory hepatic and renal function, adequate clinical performance status, treatment with an antiretroviral regimen that included either ritonavir or indinavir for at least 8 weeks prior to study enrollment and agreement to continue on a stable regimen throughout the study, ability and willingness to provide written informed consent, agreement to practice medically-approved contraception.

Patients were ineligible for inclusion in the study if the following exclusion criteria were met: concurrent pregnancy or breast feeding, concurrent use of other colony stimulating factors or cytokines (other than erythropoietin), life-expectancy <90 days, concurrent radiation or systemic cancer chemotherapy (or within 2 weeks prior to study entry), inability to self-administer or arrange for administration of subcutaneous injections, significant cardiac disease, prior history of adverse reaction to yeast-derived rhu GM-CSF which would prohibit retreatment, active infection (AIDS-related or not) requiring acute systemic therapy within 8 weeks prior to study enrollment, vaccination of any kind within 8 weeks of study enrollment.

Study participants were randomly assigned to receive either active GM-CSF or placebo. Patients were instructed in methods for self-administration of study medication and received preloaded syringes or vials with empty syringes for home use.

The formulation of recombinant human GM-CSF utilized in this clinical trial was LEUKINE® (commercially available from Immunex Corporation, Seattle, Wash.). LEUKINE® and placebo were supplied as lyophilized powders. Both LEUKINE® and placebo were reconstituted by the aseptic injection of Bacteriostatic Water for Injection, USP, containing 0.9% benzyl alcohol. The placebo control for the subject study was a sterile lyophilized preparation containing only the inactive excipients present in the LEUKINE® preparation. These were 40 mg mannitol, USP; 10 mg sucrose, NF; and 1.2 mg TRIS (tromethamine), USP; per vial of study drug. Vials containing placebo were labeled in a fashion identical to vials containing LEUKINE®. Vials of placebo and LEUKINE® were stored refrigerated at 2–8° C. (36–46° F.).

Patients assigned randomly to treatment Group I received blinded subcutaneous injections of active reconstituted lyophilized LEUKINE® in a fixed dose of 250 mcg in a volume of 0.5 mL three times per week for eight weeks (24 doses), while patients assigned to treatment Group II received blinded subcutaneous injections of 0.5 mL of the placebo according to the same schedule. Safety evaluations included monitoring of HIV viral load by sensitive RNA-PCR methods and clinical monitoring for HIV-related illnesses.

At 2, 4 and 8 weeks after the start of study drug and at follow-up (approximately 4 weeks after completion of study drug), patients were examined, their medical histories were updated, and samples were taken for laboratory studies. A central laboratory was utilized for HIV quantification laboratory tests in order to standardize procedures and minimize variability. These samples were batched by subject to further reduce variability and, with exception of the screening RNA-PCR, results were not available to the study site until after the completion of the study. All other laboratory evaluations were analyzed at licensed laboratories near the study site. Samples for these other tests were drawn at screening, baseline (pre-treatment), week 2, week 4, week 8, and 4 weeks post-discontinuation. These other laboratory evaluations included: Complete blood count (CBC) with differential, platelet count, serum chemistries (electrolytes, blood urea and nitrogen (BUN), creatinine, bilirubin, aspartate amino transaminase (AST), alkaline phosphatase), CD3/CD4/CD8 lymphocyte absolute counts and percentage of total lymphocytes. Additionally, plasma was saved for future cytokine analyses. A single urinalysis was done at baseline to document eligibility.

Results of the Study

The results for individual patients are summarized in the following Table 1A (placebo treatment) and Table 1B (GM-CSF treatment). These results are summarized in the following Table 2.

It is apparent that within the placebo arm of the study (Table 1A), the median values for $CD4^+$ T-lymphocyte counts changed very little throughout the course of treatment, and by the time of the post-treatment evaluation, were slightly lower than the baseline $CD4^+$ T-lymphocyte level. In contrast, the median values for $CD4^+$ T-lymphocyte counts for the GM-CSF arm of the study (Table 1B) were increased at all of the evaluation points and overall to a higher degree than in the placebo group. With respect to individual patients, only three (101/RI, 103/RI and 110/RI) of the ten patients in the placebo arm (30%) experienced an increase in $CD4^+$ lymphocyte counts greater than or equal to 30% through week 8, while six (104/RI, 107/RI, 107/RI, 109/RI, 111/RI, 204/RI, and 207/RI) of the ten patients (60%) receiving GM-CSF experienced an increase in $CD4^+$ lymphocyte counts greater than or equal to 30% through week 8. Thus, twice as many patients in the GM-CSF arm of the study experienced clinically significant increases in $CD4^+$ lymphocyte counts as compared to the placebo arm of the study.

The absolute data shown in Table 2 are summarized in Tables 1A and 1B as changes in $CD4^+$ lymphocyte counts. In Tables 1A and 1B, "ND" mean tests were not done. In Table 2, "N" is the number of patients for whom $CD4^+$ lymphocyte counts were done at each time point, and "n" is the number of patients exhibiting a change greater than or equal to 30%. No significant differences were observed between the GM-CSF group and the placebo group with respect to changes in viral load throughout the course of the study.

Thus, the results of the studies indicate that the administration of GM-CSF results in a significant increase in the overall number of $CD4^+$ lymphocyte cells without a concurrent increase in viral load.

TABLE 1A

Absolute CD4+ T-Lymphocyte Counts

Placebo Arm

| Patient #/Site | First Dose | Baseline CD4 | Week 2 CD4 | Week 4 CD4 | Week 8 CD4 | Post-Study CD4 |
|---|---|---|---|---|---|---|
| 101/RI | Nov. 18, 1996 | 10 | 46 | 35 | 35 | 59 |
| 103/RI | Jan. 23, 1997 | 47 | 89 | 71 | 108 | 105 |
| 106/RI | Feb. 18, 1997 | 90 | 92 | 56 | 81 | 50 |
| 108/RI | Feb. 25, 1997 | 386 | 292 | 328 | 454 | 368 |
| 110/RI | Mar. 2, 1997 | 231 | 397 | 296 | 317 | 302 |
| 201/NY | Sep. 4, 1996 | 502 | 602 | 647 | 592 | 541 |
| 203/NY | Sep. 4, 1996 | 87 | 88 | 71 | 66 | 61 |
| 206/NY | Sep. 19, 1996 | 437 | 388 | 439 | 402 | 399 |
| 208/NY | Jan. 21, 1997 | 389 | 428 | 378 | 454 | 374 |
| 209/NY | Feb. 18, 1997 | 248 | 228 | 259 | 220 | 166 |
| Median | | 240 | 260 | 278 | 269 | 234 |

TABLE 1B

Absolute CD4+ T-Lymphocyte Counts

GM-CSF Arm

| Patient #/Site | First Dose | Baseline CD4 | Week 2 CD4 | Week 4 CD4 | Week 8 CD4 | Post-Study CD4 |
|---|---|---|---|---|---|---|
| 102/RI | Jan. 21, 1997 | 24 | 15 | 26 | 18 | 136 |
| 104/RI | Jan. 27, 1997 | 136 | 157 | 182 | 176 | 200 |
| 105/RI | Feb. 6, 1997 | 276 | 229 | 356 | 238 | 208 |
| 107/RI | Jan. 25, 1997 | 383 | 304 | 477 | 750 | 373 |
| 109/RI | Mar. 3, 1997 | 65 | 227 | 31 | 76 | 77 |
| 111/RI | Mar. 20, 1997 | 590 | 979 | 725 | 1014 | 659 |
| 202/NY | Nov. 4, 1996 | 152 | 77 | 91 | 84 | 199 |
| 204/NY | Nov. 5, 1996 | 91 | ND | 219 | 162 | 161 |
| 205/NY | Nov. 7, 1996 | 24 | 25 | 12 | 21 | 11 |
| 207/NY | Dec. 31, 1996 | 40 | 26 | 61 | 29 | 33 |
| Median | | 114 | 157 | 137 | 123 | 180 |

TABLE 2

Change in CD4+ T-Lymphocyte Counts Relative to Baseline

| | | PLACEBO | GM-CSF |
|---|---|---|---|
| WEEK 2 | Mean (Sd) | 22 (74) | 39 (150) |
| | Median | 19 | −9 |
| | Min - Max | −94–166 | −79–389 |
| | No. Patients | 10 | 9 |
| WEEK 4 | Mean (Sd) | 15 (57) | 40 (68) |
| | Median | 7 | 34 |
| | Min - Max | −58–145 | −61–135 |
| | No. Patients | 10 | 10 |
| WEEK 8 | Mean (Sd) | 30 (50) | 79 (172) |
| | Median | 43 | 4 |
| | Min - Max | −35–90 | −68–424 |
| | No. Patients | 10 | 10 |
| WEEK 12 | Mean (Sd) | 0 (51) | 28 (54) |
| | Median | −17 | 30 |
| | Min - Max | −82–71 | −68–112 |
| | No. Patients | 10 | 10 |
| MAXIMUM CHANGE > 30% THRU WEEK 8 | n/N (%) | 3/10 (30%) | 6/10 (60%) |
| MAXIMUM CHANGE > 30% THRU WEEK 12 | n/N (%) | 3/10 (30%) | 8/10 (80%) |

While the preferred embodiment of the invention has been illustrated and described, it will be appreciated that various changes can be made therein without departing from the spirit and scope of the invention.

We claim:

1. A method for treating an HLV-infected patient consisting of administering a combination of one protease inhibitor selected from the group consisting of indinavir, nelfinavir, ritonavir and saquinavir, at least one additional antiretroviral agent that is selected from the group consisting of didanosine, lamivudine, stavudine, dalcitabine and a non-nucleoside reverse transcriptase inhibitor, and human recombinant GM-CSF, wherein said combination is administered for a time sufficient to induce an increase of at least 30% in the patient's CD4+ T-lymphocyte count, and further wherein said patient has received indinavir, nelfinavir, ritonavir or saquinavir for a minimum of eight weeks prior to receiving a first dose of GM-CSF.

2. The method of claim 1, wherein the GM-CSF is administered by subcutaneous injection at a dose of 100–250 $\mu$g two times per week or three times per week.

3. A method for treating an HIV-infected patient, comprising concurrent administration of human GM-CSF and one protease inhibitor that is selected from the group consisting of indinavir, nelfinavir, ritonavir and saquinavir, wherein said patient has received said protease inhibitor for a minimum of eight weeks prior to receiving a first dose of GM-CSF, and further wherein the QM-CSF is administered for a time sufficient to induce an increase of at least 30% in the patient's CD4+ T-lymphocyte count.

4. A method according to claim 3, wherein the GM-CSF is human recombinant (GM-CSF.

5. A method according to claim 4, wherein the human recombinant GM-CSF consists of a single 127 amino acid glycoprotein that differs from endogenous human GM-CSF by a leucine instead of a proline at position 23.

6. The method of claim 3, wherein the (GM-CSF is administered by subcutaneous injection at a dose of 100–250 $\mu$g two times per week or three times per week.

* * * * *